United States Patent
Robinson et al.

(10) Patent No.: US 7,403,123 B2
(45) Date of Patent: Jul. 22, 2008

(54) METHOD AND APPARATUS FOR DISPLAYING A PATIENT WORKLIST

(75) Inventors: Scott William Robinson, Bayside, WI (US); Kira Alexander Raichert, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 131 days.

(21) Appl. No.: 11/241,432

(22) Filed: Sep. 30, 2005

(65) Prior Publication Data

US 2007/0075867 A1   Apr. 5, 2007

(51) Int. Cl.
*G08B 23/00*    (2006.01)

(52) U.S. Cl. ............... 340/573.1; 340/506; 340/3.1; 340/825.36; 340/825.49; 705/2; 705/3

(58) Field of Classification Search ............ 340/573.1, 340/506, 3.1, 825.36, 825.49; 705/2, 3
See application file for complete search history.

(56) References Cited

U.S. PATENT DOCUMENTS

| | | | |
|---|---|---|---|
| 5,146,562 A | | 9/1992 | Kukla |
| 5,447,164 A | | 9/1995 | Shaya et al. |
| 5,772,585 A | * | 6/1998 | Lavin et al. ........... 600/300 |
| 5,781,442 A | * | 7/1998 | Engleson et al. ........... 700/214 |
| 6,406,426 B1 | * | 6/2002 | Reuss et al. ........... 600/300 |
| 6,757,416 B2 | | 6/2004 | Kleiman et al. |
| 6,956,572 B2 | * | 10/2005 | Zaleski ........... 345/440.2 |
| 7,107,547 B2 | | 9/2006 | Cule et al. |
| 2003/0061073 A1 | | 3/2003 | Seow et al. |
| 2004/0262377 A1 | | 12/2004 | Matz |
| 2005/0177050 A1 | | 8/2005 | Cohen |
| 2006/0277070 A1 | | 12/2006 | Hungerford et al. |

* cited by examiner

*Primary Examiner*—Daryl C Pope
(74) *Attorney, Agent, or Firm*—Armstrong Teasdale LLP

(57) ABSTRACT

An apparatus displaying a patient worklist includes at least one processor, a pointing device, a display screen having a viewing area, and memory, and is configured to store patient information, including cautionary information and scheduled medical procedures, in the memory. The apparatus is further configured to display the patient information on the display screen in a worklist of patient listings for individual patients. The displayed patient information includes scheduled medical procedures for each patient and a visual cautionary indication in a consistent position relative to each patient in the worklist for whom cautionary information is stored. The apparatus is also configured to open a preview pane on the display screen entirely within the viewing area of the display screen when the visual cautionary indication is selected by the pointing device. The preview pane contains cautionary details associated with the corresponding patient for the selected visual cautionary indication.

23 Claims, 5 Drawing Sheets

| SORT BY | NAME ▽ | LAST: | | FIRST: | | ○ DETAILS | |
|---|---|---|---|---|---|---|---|
| CAUTION | DATE | NAME | ID | ACCESSION | REF. PHYS. | MODALITY | DESCRIPTION | ARRIVAL |
| | 1/12/2005 | ANDERS, THOMAS | 123-34-4567 | 123456789 | SMITH, JOHN | XR | WRIST 4 VIEW | SCHEDULED |
| | 1/12/2005 | BERNARD, ALAN | 234-45-6789 | 222222222 | JONES, FRED | XR | C/TH SPINE | ARRIVED |
| | 1/12/2005 | CAPP, JOSEPHINE | 345-56-7890 | 321321321 | GOODE, LISA | XR | C/TH SPINE | SCHEDULED |
| | 1/12/2005 | DOBBS, JANE | 456-67-1234 | 432432432 | GOODE, LISA | XR | NECK | SCHEDULED |
| | 1/12/2005 | GRANT, LEWIS | 150-15-1515 | 324567890 | SMITH, JOHN | XR | WRIST 4 VIEW | ARRIVED |
| | 1/12/2005 | HASS, LINDA | 592-50-1414 | 782931234 | GOODE, LISA | XR | NECK | ARRIVED |
| | 1/12/2005 | LANE, FRANK | 674-43-4321 | 910321031 | SMITH, JOHN | XR | C/TH SPINE | SCHEDULED |
| | 1/12/2005 | MUSTARD, GENE | 180-80-1280 | 712368321 | JONES, FRED | XR | NECK | SCHEDULED |
| | 1/12/2005 | OLANDER, LISA | 777-60-7111 | 617342194 | REID, ERICA | XR | WRIST 4 VIEW | ARRIVED |
| | 1/12/2005 | PECK, MICHELLE | 490-55-3331 | 819328132 | REID, ERICA | XR | C/TH SPINE | ARRIVED |
| | 1/12/2005 | TROY, HELEN | 821-12-3241 | 558329438 | GOODE, LISA | XR | WRIST 4 VIEW | ARRIVED |
| | 1/12/2005 | VICKERS, STEVE | 345-60-0913 | 471839512 | SMITH, JOHN | XR | NECK | SCHEDULED |
| BYPASS WORKLIST... | | RIS | | SEARCH RIS... | | | START EXAM |

METHOD AND APPARATUS FOR DISPLAYING A PATIENT WORKLIST

BACKGROUND OF THE INVENTION

This invention relates generally to medical patient worklist applications and more particularly to methods and apparatus for displaying cautionary information on such worklists.

Existing worklist applications are geared toward showing a list of patient names and a number of additional details. Occasionally they do contain cautionary information related to medical conditions e.g. allergies and/or pregnancies. The cautionary information could appear anywhere in the table, including outside of the primary viewing area, and may be divided into several columns (e.g. an allergy column, a pregnancy column, a pre-medication column, etc.). Inconsistencies in the display of cautionary information may require increased attention on the part of a user of this information and, in some cases, may require the user to scroll the display screen or open a sub-window in order to locate and read all of the cautionary information.

BRIEF DESCRIPTION OF THE INVENTION

In one aspect, some configuration of the present invention therefore provide an apparatus that includes at least one processor, a pointing device, a display screen having a viewing area, and memory. The apparatus is configured to store patient information, including cautionary information and scheduled medical procedures, in the memory. The apparatus is further configured to display the patient information on the display screen in a worklist of patient listings for individual patients, wherein the displayed patient information includes scheduled medical procedures for each patient and a visual cautionary indication in a consistent position relative to each patient in the worklist for whom cautionary information is stored. The apparatus is also configured to open a preview pane on the display screen entirely within the viewing area of the display screen when the visual cautionary indication is selected by the pointing device. The preview pane contains cautionary details associated with the corresponding patient for the selected visual cautionary indication.

In another aspect, some configurations of the present invention provide a method for displaying patient data. The method includes storing patient information, including cautionary information and scheduled medical procedures, in a memory of a computing apparatus, displaying the patient information on a display screen of the computing apparatus in a worklist of patient listings for individual patients, wherein the displayed patient information includes scheduled medical procedures for each patient and a visual cautionary indication in a consistent position relative to each patient in the worklist for whom cautionary information is stored. The method also includes opening a preview pane on the display screen entirely within a viewing area of the display screen when the visual cautionary indication is selected by a pointing device of the computing apparatus, wherein the preview pane contains cautionary details associated with the corresponding patient for the selected visual cautionary indication.

In yet another aspect, some configurations of the present invention provide a machine-readable medium having instructions recorded thereon to instruct a processor to store patient information, including cautionary information and scheduled medical procedures, in a memory of a computing apparatus. The instructions also instruct the processor to display the patient information on a display screen of the computing apparatus in a worklist of patient listings for individual patients, wherein the displayed patient information includes scheduled medical procedures for each patient and a visual cautionary indication in a consistent position relative to each patient in the worklist for whom cautionary information is stored. The instructions further instruct the processor to open a preview pane on the display screen entirely within a viewing area of the display screen when the visual cautionary indication is selected by a pointing device of the computing apparatus, wherein the preview pane contains cautionary details associated with the corresponding patient for the selected visual cautionary indication.

Various configurations of the present invention will be seen to assist caregivers in becoming aware of existing cautionary medical information prior to administering medical procedures.

BRIEF DESCRIPTION OF THE DRAWINGS

FIG. 2 is an example of a displayed worklist of some configurations of the present invention, showing a visual cautionary indicator beside on of the names in the worklist.

FIG. 3 is an example of a preview pane of some configurations of the present invention.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features. Also as used herein, a "processor" includes within its scope a computer or computing apparatus, which may include plural processors, as well as individual CPUs.

Technical effects of the present invention include the highly visible display of cautionary information to caregivers in a consistent manner.

Configurations of the present invention include standalone workstations or computers, imaging or other medical apparatus having computers or computer control, and machine-readable media on which instructions are recorded that are configured to instruct a processor to perform configurations of the methods discussed herein. As a non-limiting example, a configuration is described herein that is a Computed Tomography (CT) imaging system. However, the extension of the explanation to configurations that comprise other medical apparatus or standalone workstations or computers or other modalities will be straightforward to one skilled in the art, once an understanding of the examples explained herein is achieved. In particular, it is intended that various worklist configurations of the present invention are capable of cross-modality use, including, for example, CT, magnetic resonance imaging (MR), CT/PET (positron emission tomography), and nuclear medicine capability.

Figure 1:
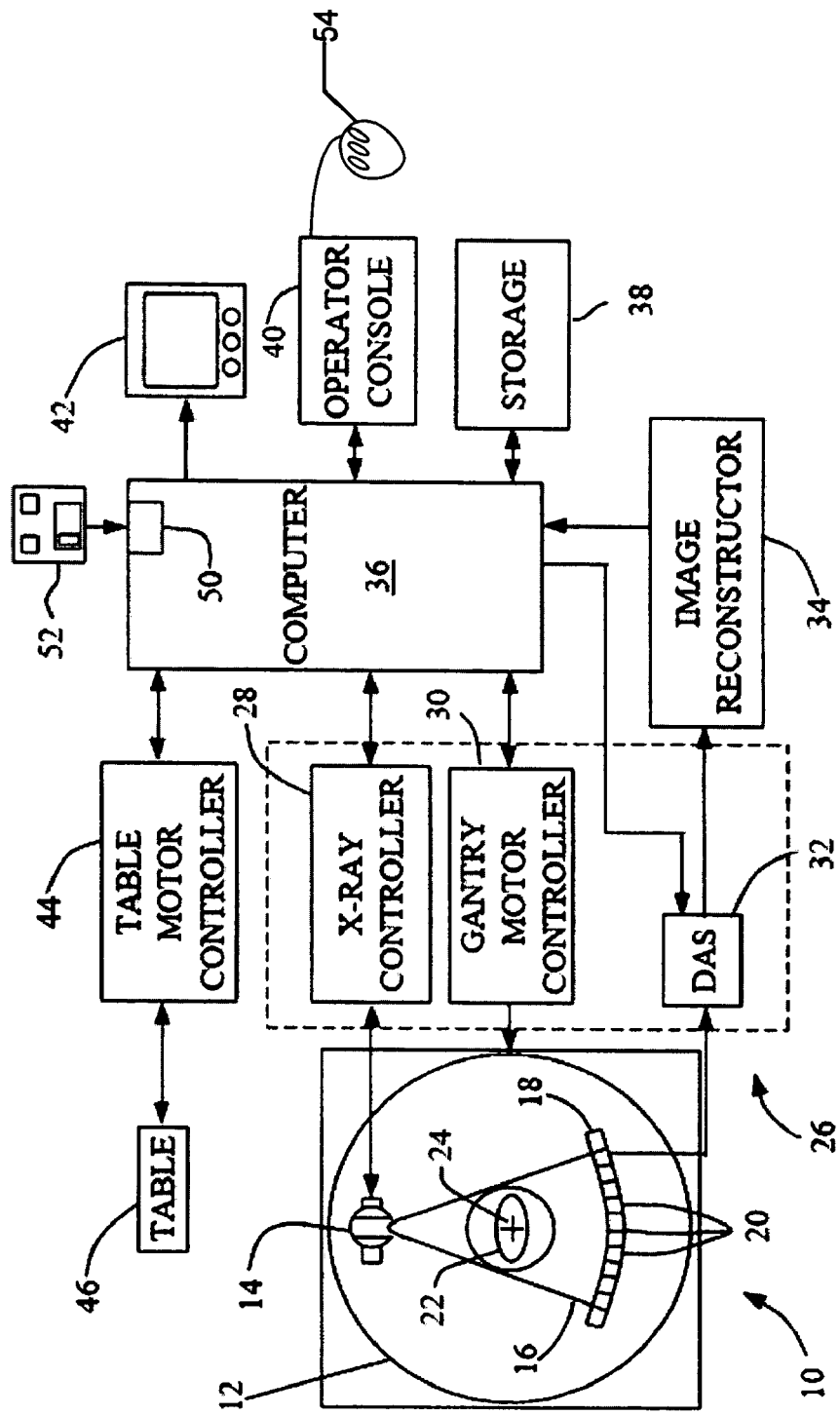
FIG. 1 is a pictorial block diagram representative of some configurations of the present invention.

Referring to FIG. 1, a Computed Tomography (CT) imaging system 10, is shown in block diagram form as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36. For purposes of the present invention, image reconstructor 34 may be considered as part of computer 36 even if image reconstructor 34 is provided as specialized hardware.

Computer 36, which may include a keyboard or other use input device, also receives commands and scanning parameters from an operator via console 40. An associated cathode ray tube display, liquid crystal display, plasma display, or any other suitable type of visual display 42 allows the operator to observe the reconstructed image and other data, such as patient worklists, from computer 36. Computer 36 is also supplied with a pointing device 54, non-exclusive examples of which include a mouse (as shown), a trackball, a light pen, a touch sensitive screen on display 42, or software modules that allow a keyboard of the computer to operate as a pointing device.

The operator supplied commands and parameters are used by computer 36 to provide control signals and information to DAS 32, x-ray controller 28, and gantry motor controller 30. In addition, computer 36 operates a table motor controller 44, which controls a motorized table 46 (on which patient or object 22 is resting) to position patient 22 in gantry 12. Particularly, table 46 moves portions of patient 22 through an opening in gantry 12.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer and the term processor are not limited to just those integrated circuits referred to in the art as computers or processors, but broadly refers to computers, processors, workstations, microcontrollers, microcomputers, programmable logic controllers, application specific integrated circuits, and other programmable circuits, and these terms are used interchangeably herein.

Figure 3:
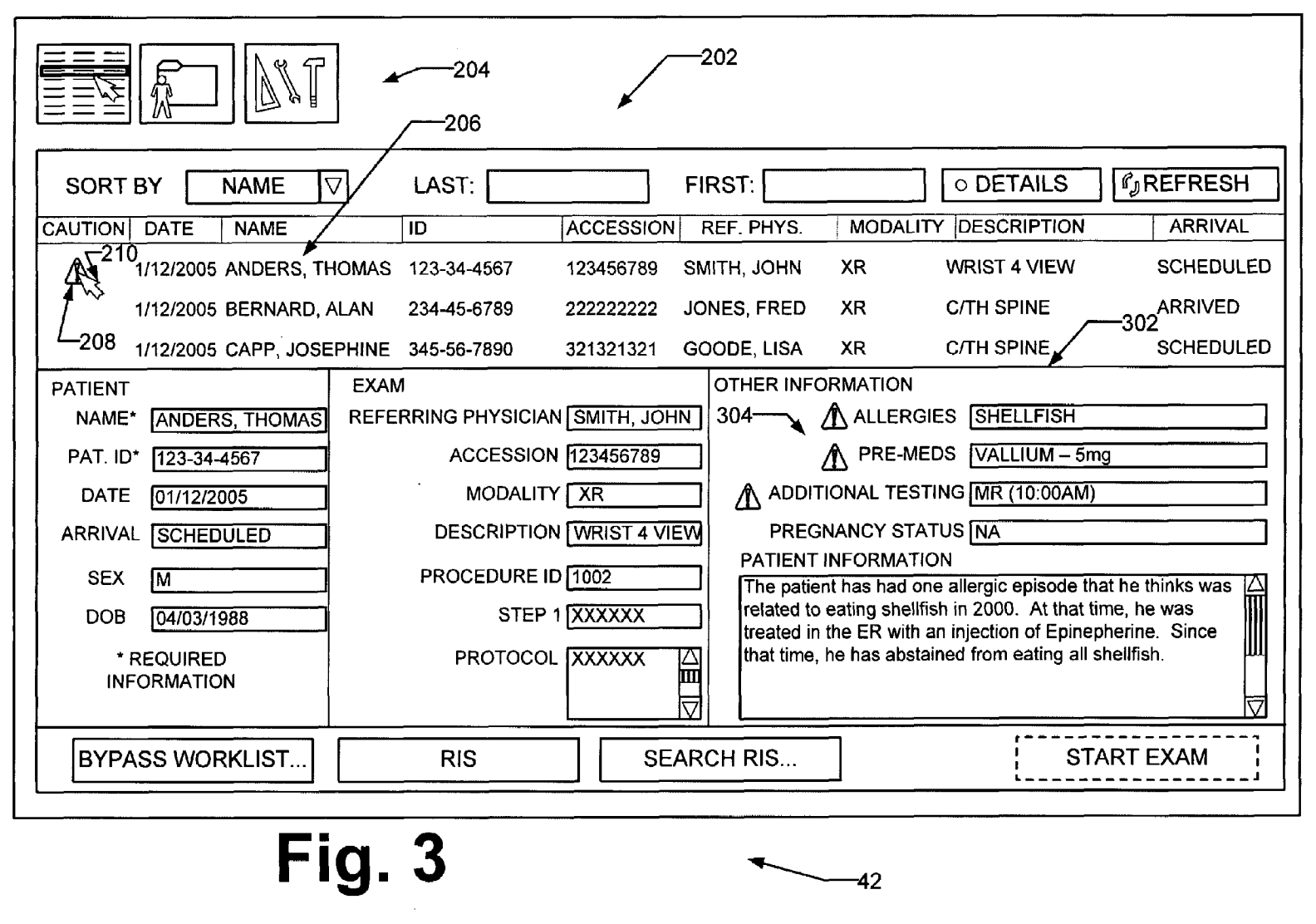

Some configurations of the present invention provide a combination of a visual cautionary indicator (which may be an icon) and detailed preview pane. For example, and referring to FIG. 2, some configurations of the present invention display a worklist 202 on display screen 42. The worklist may include visual buttons with icons, such as 204, and/or other conventional controls for navigation and other purposes. Worklist 202 includes a list of names 206 of patients as well as (for example) medical information, schedule dates, patient ID numbers acquired from a radiology information system (RIS), accession numbers, names of referring physicians, modality information (e.g., the type of imaging or other medical apparatus to be used for the patient), a description of the scheduled procedure, and whether a patient has arrived yet or is scheduled but not yet arrived. A cautionary indication such as a cautionary icon 208 is prominently displayed in (for example) a first column of worklist 202. Cautionary icon 208 provides a single visual indication that pre-existing medical conditions exist. In some configurations of the present invention and referring to FIG. 3, when icon 208 is selected (for example, by using pointing device 54 to hover pointer 210 over icon 208 and clicking on pointing device 54, this selection causes a preview pane 302 to open. Preview pane 302 is disposed entirely within the display area of display screen 42, so that a user need not scroll to see information contained therein. Preview pane 302 reveals detailed information 304 that is stored in a memory of computer 36 for a corresponding patient 206 concerning pre-existing medical conditions that may pose a potential risk to the patient in the context of the scheduled medical procedure.

More particularly, in a conventional manner, a user operates computer 36 to store patient information, including any cautionary information and scheduled medical procedures, in a memory of computer 36, for example, storage system 38. Typically, some, but not all patients will have corresponding cautionary information stored. Possibly (but not necessarily) at a different time, a user (possibly different from the one storing the information) will issue a command to computer 36 to display patient information on display screen 42 in a worklist 202 of patient listings for individual patients. Worklist 202 may be sorted (for example) by name, date, or any other stored record. If the worklist is too large for display screen 42, one or more scrollbar controls (not shown in the Figures for this purpose) may be displayed to enable the user to review the entire worklist. Worklist 202 includes scheduled medical procedures for each patient. (Configurations of the present invention need not exclude the presentation of other displays the do not include scheduled medical procedures.) Worklists 202 display a visual cautionary indication 208 in a consistent position relative to each patient listing 206 when cautionary information is stored for a corresponding patient ("Anders, Thomas" in FIG. 2). Using pointing device 54 to select (e.g., point and click on) visual cautionary indication 208 brings up a preview pane 302 entirely within the viewing area of display screen 42. Preview pane 302 contains cautionary details associated with the corresponding patient (i.e., the one whose name appears next to the selected cautionary indication, which, in the illustrated case, is "Thomas Anders").

In some configurations of the present invention, cautionary indication 208 is an icon, for example, an exclamation point enclosed in a triangle. Also, in some configurations of the present invention, each displayed preview pane, regardless of which patient's cautionary indication 208 is selected, contains cautionary details 304 in the same location of display screen 42, so that a user need not scan the entire display or scroll the display to locate this information. Also, some configurations of the present invention are configured to selectively generate an image of a patient on display screen 42. For example, once worklist 202 is read and any cautionary information 304 understood, a user may operate CT imaging system 10 to produce a radiation beam 16 that passes through a patient 22 (for example, "Thomas Anders," at his scheduled appointment), and use the detected radiation to generate an image of patient 22 on screen 42. The image is "selectively" generated in that computer 36 in some configurations selectively displays either worklist 202 or the image, as instructed by a user.

Figure 4:
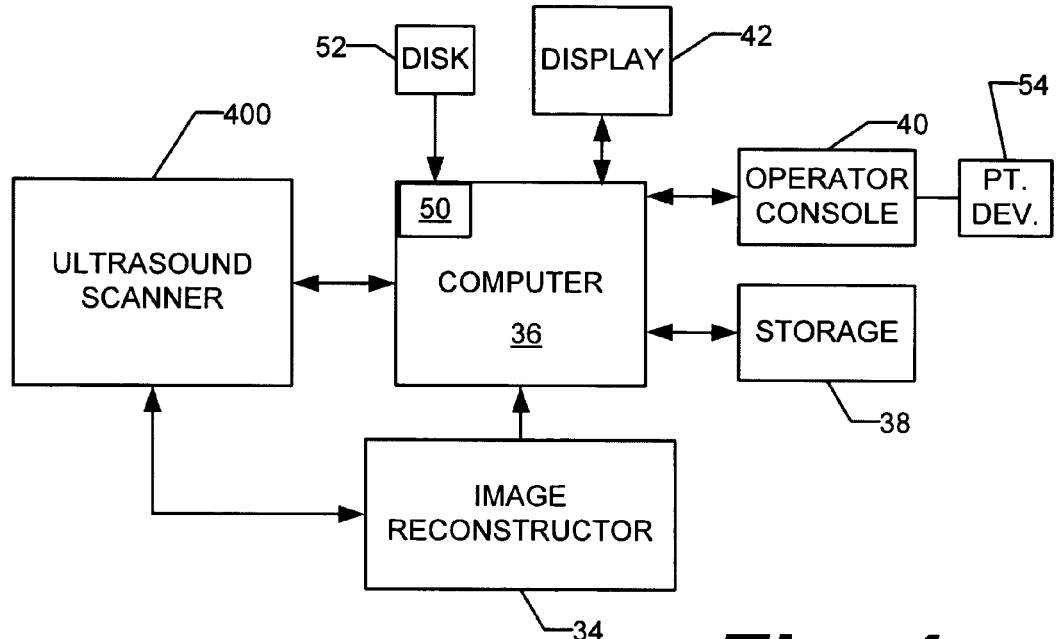
FIG. 4 is a pictorial block diagram representative of some configurations of the present invention embodied in an ultrasound imaging apparatus.
Figure 5:
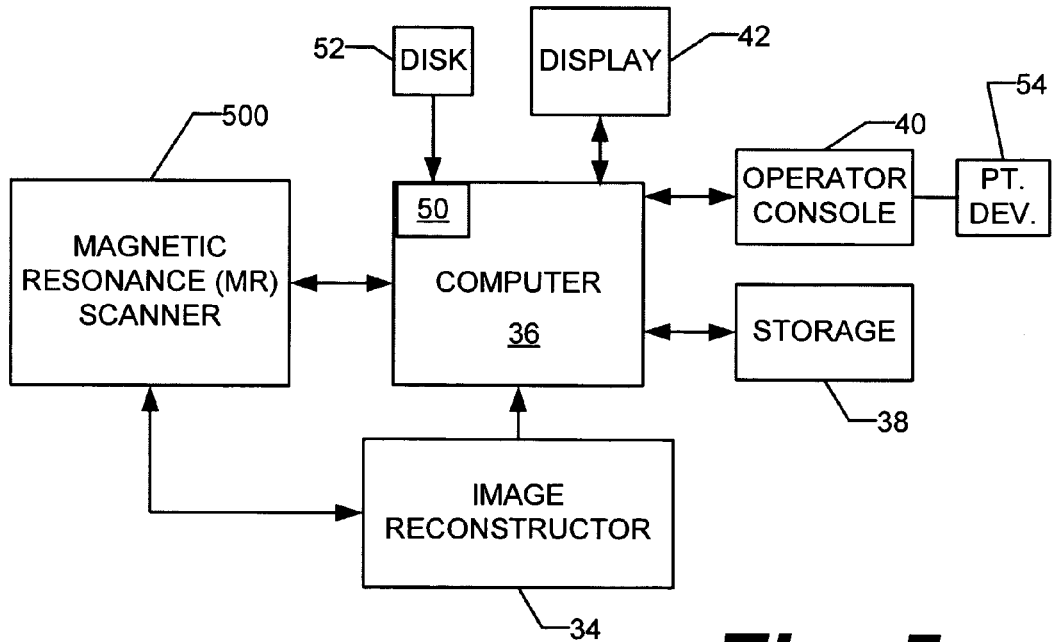
FIG. 5 is a pictorial block diagram representative of some configurations of the present invention embodied in a nuclear magnetic resonance imaging apparatus.

As indicated above, configurations of the present invention need not be embodied as CT imaging apparatus, and may comprise stand-alone computers or workstations, machine-readable media having recorded instructions thereon, or other medical devices. For example, a configuration of the present invention may be configured to detect either radiation passing through a patient (e.g., CT, X-ray, or ultrasound imaging systems with detectors configured to detect ultrasound radiation passing through a patient), or radiation generated or induced within a patient (e.g., PET detectors or NMR imaging systems), and need not be limited to imaging systems. Also, some configurations of the present invention are embodied in other medical apparatus. For example, and referring to FIG. 4, a configuration of the present invention can be embodied in an ultrasound imaging apparatus using an ultrasound scanner 400, or referring to FIG. 5, a configuration of the present invention can be embodied in a nuclear magnetic resonance (NMR) imaging device using an NMR scanner 500. Furthermore, the apparatus can be configured to carry out the medical procedure for such apparatus, whether it be an x-ray scan, a CT scan, an MR scan, or an ultrasound.

Figure 6:
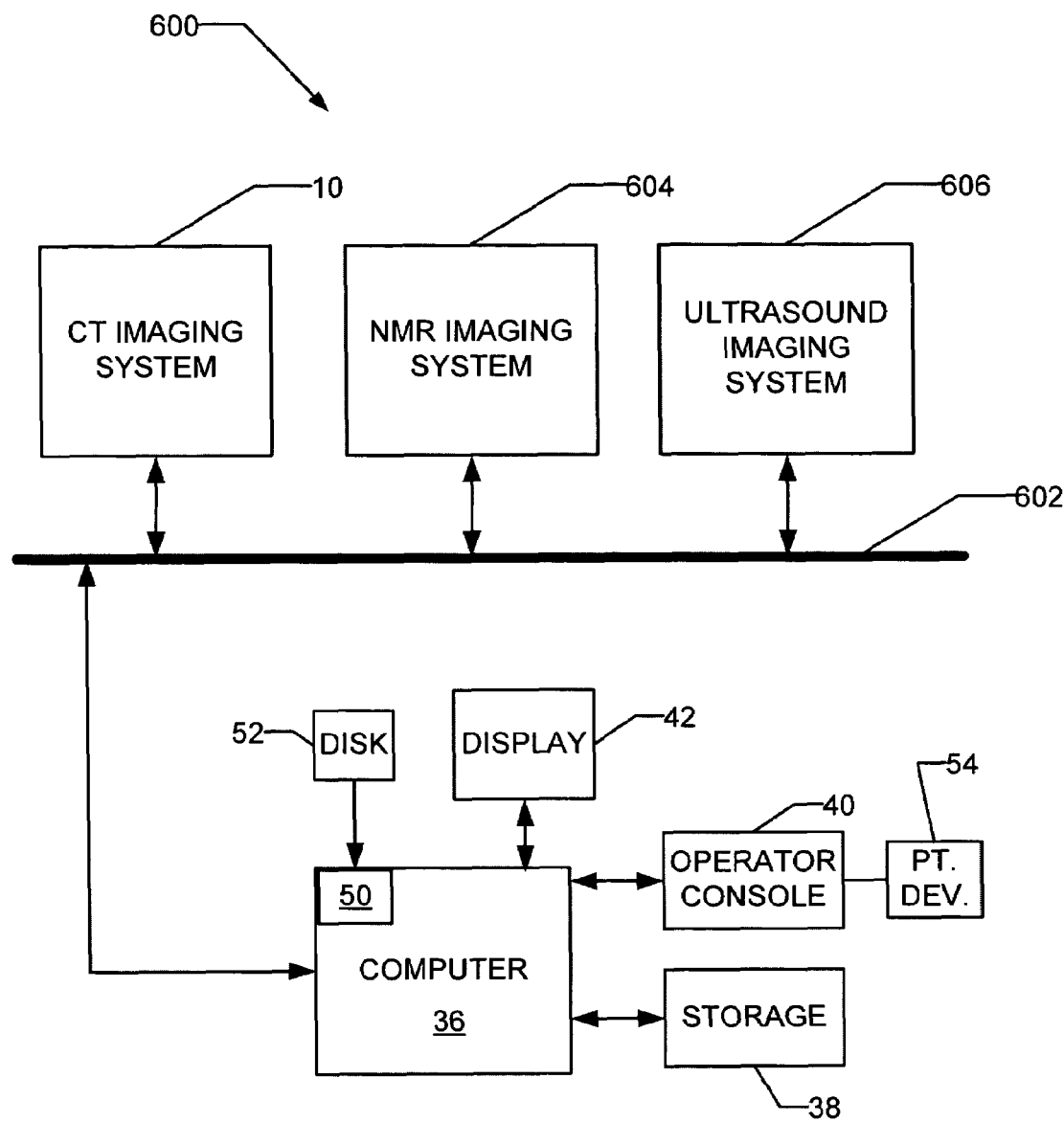
FIG. 6 is a pictorial block diagram representative of a networked configuration of the present invention.

Also, in some configurations and referring to FIG. 6, a system 600 is provided in which a computer 36 (which may be a stand-alone device or computer embodied in a medical device) configured as described herein for storing patient information communicates over a network 602 having a plurality of medical devices (e.g., CT imaging system 10, NMR imaging system 604 and/or ultrasound imaging system 606, and/or others). Information concerning procedures for patients using the medical devices communicating over network 602 is stored in a memory of computer 36, and answers to requests to display patient information are displayed on display 42. In some configurations, information regarding the patient is made available to medical devices communicating on network 602 and displayed on a display local to the medical device in the same manner as on display 42. Also in some configurations, the information in computer 36 is remotely available at other locations on network 600, and computer 36 is used as a database to provide patient information on that network to be displayed in the manner described herein.

It will thus be appreciated that configurations of the present invention assist caregivers in becoming aware of existing cautionary medical information prior to administering medical procedures.

While the invention has been described in terms of various specific embodiments, those skilled in the art will recognize that the invention can be practiced with modification within the spirit and scope of the claims.

What is claimed is:

1. An apparatus comprising a radiation detection system configured to detect at least either radiation passing through a patient or radiation generated or induced within a patient at least one processor, a pointing device, a display screen having a viewing area, and memory, said apparatus configured to:
   store patient information, including cautionary information and scheduled medical procedures, received as input from an operator or from a radiology information system, in said memory;
   display said patient information on said display screen in a worklist of patient listings for individual patients, said displayed patient information including scheduled medical procedures for each patient and a visual cautionary indication in a consistent position relative to each said patient in the worklist for whom cautionary information is stored; and
   open a preview pane on said display screen entirely within the viewing area of the display screen upon selecting the visual cautionary indication with the pointing device, said preview pane containing cautionary details associated with the corresponding patient for the selected visual cautionary indication;
   selectively generate an image of the patient on the display screen using the detected radiation.

2. An apparatus in accordance with claim 1 wherein said visual cautionary indication is an icon.

3. An apparatus in accordance with claim 1 wherein each said displayed preview pane contains cautionary details in the same location independent of which said visual cautionary indicator is selected.

4. An apparatus in accordance with claim 3 wherein the visual cautionary indication is an icon.

5. An apparatus in accordance with claim 1 wherein the image processing system includes an x-ray source and a detector array configured to detect radiation passing through a patient.

6. An apparatus in accordance with claim 5 configured to generate a computed tomographic image of the patient.

7. An apparatus in accordance with claim 1 wherein the image processing system includes an ultrasound emitter and detector configured to detect reflected or transmitted ultrasound radiation through the patient.

8. An apparatus in accordance with claim 1 wherein the image processing system is configured to generate a nuclear magnetic resonance image of the patient.

9. An apparatus in accordance with claim 1, wherein the preview pane containing cautionary details associated with the corresponding patient is closed before selecting the visual cautionary indication used to open the preview pane.

10. A method for displaying patient data, said method comprising:
   storing patient information, including cautionary information and scheduled medical procedures, in a memory of a computing apparatus;
   displaying the patient information on a display screen of the computing apparatus in a worklist of patient listings for individual patients, wherein the displayed patient information includes scheduled medical procedures for each patient and a visual cautionary indication in a consistent position relative to each patient in the worklist for whom cautionary information is stored;
   opening a preview pane on the display screen upon selecting the visual cautionary indication with a pointing device of the computing apparatus, wherein the preview pane contains cautionary details associated with the corresponding patient for the selected visual cautionary indication, and wherein the preview pane can be viewed in its entirety without scrolling contents of the display screen;

detecting either radiation passing through a patient, radiation generated or induced within a patient, or both; and selectively displaying an image of the patient on the display screen using the detected radiation.

11. A method in accordance with claim 10 wherein the visual cautionary indication is an icon.

12. A method in accordance with claim 10 wherein each displayed preview pane contains cautionary details in the same location independent of which visual cautionary indicator is selected.

13. A machine-readable medium having instructions recorded thereon to instruct a processor to:

store patient information, including cautionary information and scheduled medical procedures, in a memory of a computing apparatus;

display the patient information on a display screen of the computing apparatus in a worklist of patient listings for individual patients, wherein the displayed patient information includes scheduled medical procedures for each patient and a visual cautionary indication in a consistent position relative to each patient in the worklist for whom cautionary information is stored;

open a preview pane on the display screen upon receiving a selection of the visual cautionary indication, wherein the preview pane contains cautionary details associated with the corresponding patient for the selected visual cautionary indication and the preview pane is entirely contained within the display screen;

operate at least a radiation detector to detect either radiation passing through a patient, radiation generated or induced within a patient, or both; and selectively display an image of the patient on the display screen using the detected radiation.

14. A machine-readable medium in accordance with claim 13 wherein the visual cautionary indication is an icon.

15. A machine-readable medium in accordance with claim 14 wherein said instructions include instructions for each displayed preview pane to contain cautionary details in the same location independent of which visual cautionary indication is selected.

16. An apparatus comprising:

a display screen having a viewing area; and a computer programmed to:

determine a number of patients scheduled for a medical procedure;

identify at least one patient of the number of patients having cautionary information associated therewith;

populate the viewing area with a list of the number of patients awaiting a medical procedure with a single visual identifier assigned to each of the patients in the list having cautionary information associated therewith;

operate at least a radiation detector to detect either radiation passing through a patient, radiation generated or induced within a patient, or both; and selectively display an image of the patient on the display screen using the detected radiation.

17. The apparatus of claim 16 wherein the single visual identifier is an icon and wherein the computer is further programmed to display a preview pane in the viewing area having at least the cautionary information therein for a given patient when the single visual identifier assigned to the given patient is selected by a user.

18. The apparatus of claim 17 wherein the computer is further programmed to display the preview pane in the display area without requiring user scrolling of the preview pane.

19. The apparatus of claim 17 wherein the computer is further programmed to display the cautionary information in a dedicated location of the preview pane such that the cautionary information is consistently displayed independent of which single visual identifier is selected by a user.

20. The apparatus of claim 19 configured to carry out the medical procedure.

21. The apparatus of claim 16 wherein the computer is further programmed to access a database of stored patient information and assign the single visual identifier to a patient if the stored patient information for the patient indicates that the patient is allergic to a given medication, recently underwent a medical procedure, or is pregnant.

22. The apparatus of claim 16 wherein the computer is further programmed to display each single visual identifier in a consistent position relative to each patient listing.

23. The apparatus of claim 16 wherein the medical procedure includes one of an x-ray scan, a CT scan, an MR scan, and an ultrasound.

* * * * *